United States Patent [19]

Hironaka et al.

[11] Patent Number: 5,466,392
[45] Date of Patent: Nov. 14, 1995

[54] ORGANIC ELECTROLUMINESCENCE DEVICE AND COMPOUND HAVING AN ALUMINUM COMPLEX STRUCTURE

[75] Inventors: Yoshio Hironaka; Hiroaki Nakamura; Tadashi Kusumoto, all of Sodegaura, Japan

[73] Assignee: Idemitsu Kosan Co., Ltd., Tokyo, Japan

[21] Appl. No.: 253,052

[22] Filed: Jun. 2, 1994

[30] Foreign Application Priority Data

Jun. 2, 1993 [JP] Japan .................. 5-131875

[51] Int. Cl.$^6$ .................. C07K 11/06; C07F 5/06
[52] U.S. Cl. .................. 252/301.16; 252/301.26; 428/917; 546/6; 546/7
[58] Field of Search .................. 252/301.16, 301.26; 428/917; 546/6, 7; 313/504

[56] References Cited

U.S. PATENT DOCUMENTS

| | | | |
|---|---|---|---|
| 5,130,603 | 7/1992 | Tokailin et al. | 252/301.16 |
| 5,141,671 | 8/1992 | Bryan et al. | 546/7 |
| 5,150,006 | 9/1992 | Van Slyke et al. | 313/504 |

FOREIGN PATENT DOCUMENTS

| | | | |
|---|---|---|---|
| 579151 | 1/1994 | European Pat. Off. | 546/7 |

*Primary Examiner*—Stephen Kalafut
*Assistant Examiner*—Alan D. Diamond
*Attorney, Agent, or Firm*—Oblon, Spivak, McClelland, Maier, & Neustadt

[57] ABSTRACT

An organic electroluminescence device having excellent properties of high luminance, high efficiency of light emission and long life and a novel compound having an aluminum complex structure used as a component in said device are disclosed. The invention provides an organic electroluminescence device comprising a compound having an aluminum complex structure represented by the general formula (I):

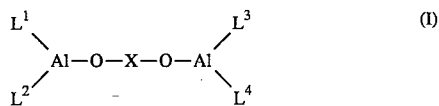

wherein X indicates —$Ar^1$—Y—$Ar^2$— or an aryl- or alkylsilylene group, $Ar^1$ and $Ar^2$ indicate each an aromatic ring, Y indicates an alkylene group, a cycloalkylene group, an alkylidene group, a cycloalkylidene group, —CO—, —O—, —S— or the like and $L^1$ to $L^4$ indicate each a ligand, such as a substituted or unsubstituted 8-quinolyloxy group or the like. The invention also provides a compound having an aluminum complex structure described above.

15 Claims, 1 Drawing Sheet

ORGANIC ELECTROLUMINESCENCE DEVICE AND COMPOUND HAVING AN ALUMINUM COMPLEX STRUCTURE

BACKGROUND OF THE INVENTION

1. Field of the Invention

The present invention relates to a novel organic electroluminescence device and a novel compound having an aluminum complex structure used in the device, and more particularly, to an organic electroluminescence device having excellent properties of high luminance, high efficiency of light emission and long life and a compound having an aluminum complex structure which provides the device with the excellent properties by using it as a component of the device.

2. Description of Related Art

Investigations to increase efficiency of light emission by forming an electron injecting and transporting layer in an electroluminescence device (hereinafter referred to as an EL device) have heretofore been made. The investigations revealed drawbacks that formation of an exciplex is observed and that life time of light emission, is short even though light emission of high luminance can be obtained. The investigations also revealed other drawbacks that cleavage between a metal electrode and an organic layer occurs after a voltage is loaded for a long time and that an organic layer or an electrode turns turbid by crystallization and luminance of the emitted light is decreased. Therefore, it has been required that occurrences of these phenomena are prevented.

As an example of a compound having a specific aluminum complex structure which is comprised in an organic EL device as a component thereof, compounds disclosed in U.S. Pat. Nos. 5,141,671 (1992) and 5,150,006 (1992) can be mentioned. These compounds are used as a material for a light emitting layer emitting blue light with doping of a polycyclic aromatic compound.

However, an aluminum-quinoline complex is used additionally as an electron injecting and transporting layer in these inventions and a drawback is found that efficiency of light emission is low when the device does not contain an electron injecting and transporting layer.

An organic EL device using a specific aluminum complex is disclosed in European Patent Application Laid-Open No. 579151A2. However, this aluminum complex is different from the compound having an aluminum complex structure disclosed in the present invention.

SUMMARY OF THE INVENTION

The present invention has the object of providing an organic EL device having excellent properties of high luminance, high efficiency of light emission and long life time, using a novel compound having an aluminum complex structure in one or both of the light emitting layer and the electron injecting and transporting layer.

As the result of extensive studies to achieve the above object by the present inventors, it was discovered that the object can be achieved by using a compound having a specific aluminum complex structure as a component of the organic EL device. The present invention has been completed on the basis of the discovery.

Thus, the present invention provides an organic electroluminescence device comprising a compound having an aluminum complex structure represented by the following general formula (I):

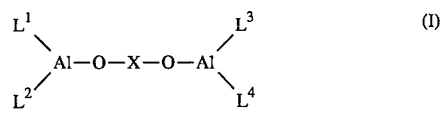

wherein X indicates a group represented by one of the formulae: $-Ar^1-Y-Ar^2-$,

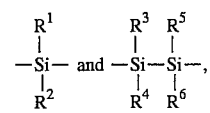

therein $Ar^1$ and $Ar^2$ indicate each independently a substituted or unsubstituted aromatic ring having 6 to 24 carbon atoms, Y is an alkylene group, a cycloalkylene group, an alkylidene group, a cycloalkylidene group, an arylenedioxy group, an alkylenedioxy group,

$-O-$, $-S-$, $-SO-$ or $-SO_2-$, and $R^1$ to $R^6$ indicate each independently an aryl group having 6 to 12 carbon atoms, an alkyl group having 1 to 12 carbon atoms or a cycloalkyl group having 5 to 12 carbon atoms; and $L^1$ to $L^4$ indicate each independently a substituted or unsubstituted ligand having one of the formulae:

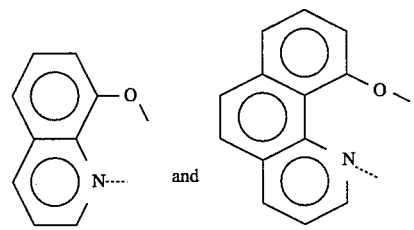

The present invention also provides a compound having an aluminum complex structure represented by the general formula (I) described above.

DESCRIPTION OF PREFERRED EMBODIMENTS

Figure 1:
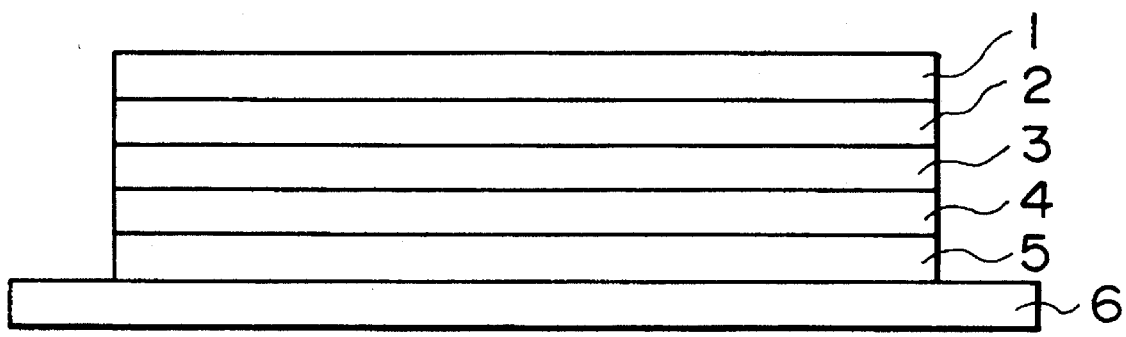
FIG. 1 shows the structure of an example of the organic EL device of the present invention. In the FIGURE, 1 indicates a cathode, 2 indicates an electron injecting and transporting layer, 3 indicates a light emitting layer, 4 indicates a hole injecting and transporting layer, 5 indicates an ITO electrode and 6 indicates a glass substrate.

The organic EL device of the present invention comprises a compound having an aluminum complex structure represented by the following general formula (I):

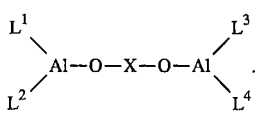 (I)

In the general formula (I), X indicates a group represented by one of the formulae: —Ar$^1$—Y—Ar$^2$,

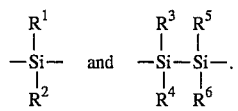

In the first formula, Ar$^1$ and Ar$^2$ indicate each independently a substituted or unsubstituted aromatic ring having 6 to 24 carbon atoms and Y indicates an alkylene group, a cycloalkylene group, an alkylidene group, a cycloalkylidene group, an arylenedioxy group, an alkylenedioxy group,

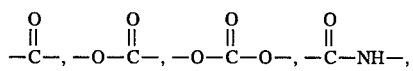

—O—, —S—, —SO— or —SO$_2$—. Preferable examples of the alkylene group are alkylene groups having 1 to 10 carbon atoms, such as methylene group, ethylene group, propylene group, butylene group, pentylene group, hexylene group, octylene group and the like. These groups may be linear or branched. Examples of the alkylidene group are groups represented by the general formula:

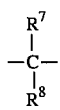

wherein R$^7$ and R$^8$ indicate each independently hydrogen atom, an alkyl group having 1 to 12 carbon atoms, a cycloalkyl group having 5 to 12 carbon atoms, an aryl group having 6 to 12 carbon atoms or trifluoromethyl group and either one of them is a group other than hydrogen atom.

Specific examples of the alkylidene group are:

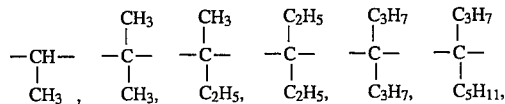

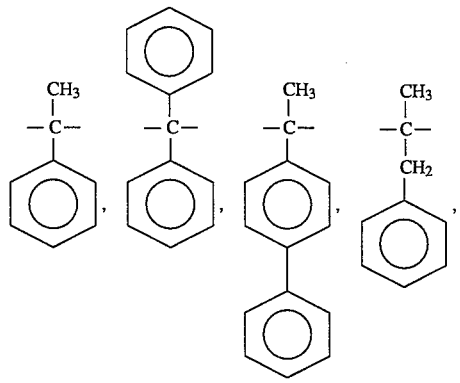

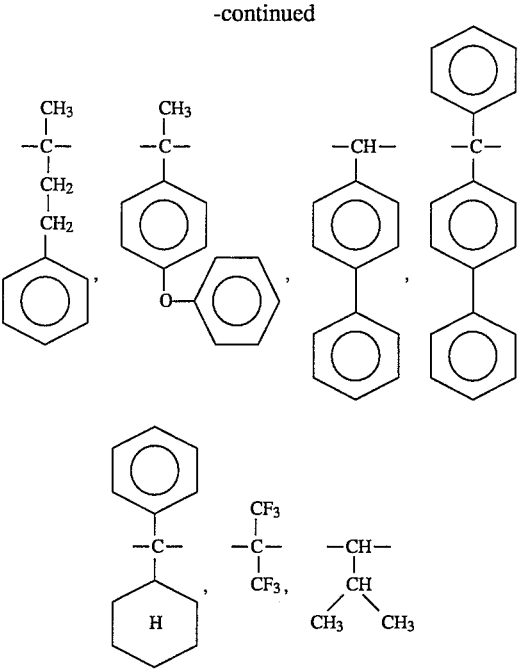

Preferable examples of the cycloalkylene group are cycloalkylene groups having 5 to 12 carbon atoms. Examples of the cycloalkylidene group, the arylenedioxy group and the alkylenedioxy group are groups represented by the following formulae:

Cycloalkylidene group

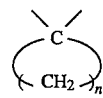

n: 4~11

Arylenedioxy group

p: 1~6

Alkylenedioxy group

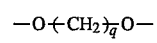

q: 1~6

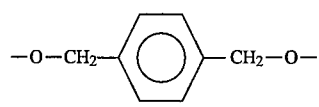

R$^1$ to R$^6$ indicate each independently an aryl group having 6 to 12 carbon atoms, an alkyl group having 1 to 12 carbon atoms or a cycloalkyl group having 5 to 12 carbon atoms.

When Ar$^1$ or Ar$^2$ is substituted, examples of the substituent are alkyl groups having 1 to 6 carbon atoms, such as methyl group, ethyl group, propyl group, isopropyl group, n-butyl group, isobutyl group, tert-butyl group, sec-butyl group, isopentyl group, tert-pentyl group, neopentyl group, hexyl group, isohexyl group and the like, alkoxy groups having 1 to 6 carbon atoms corresponding to the alkyl groups, phenyl group, cyclohexyl group, cyano group, halogen atoms (chlorine atom, fluorine atom and bromine atom), nitro group and the like.

Specific examples of X are:

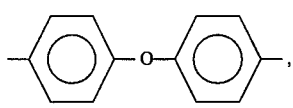

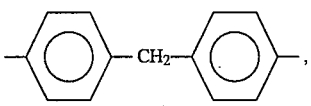

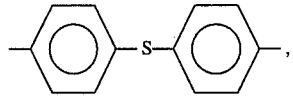

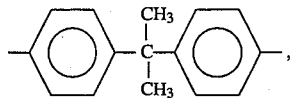

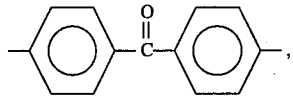

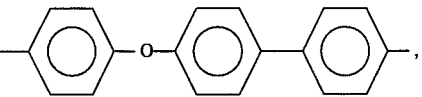

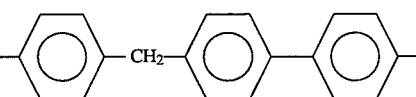

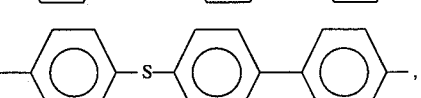

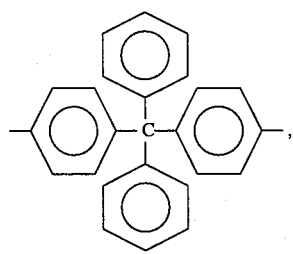

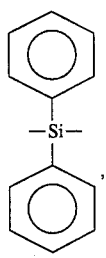  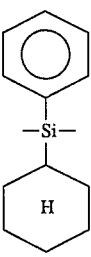 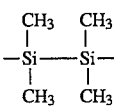

Preferable examples among them are:

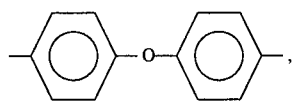

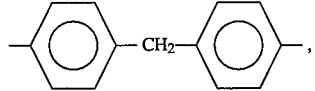

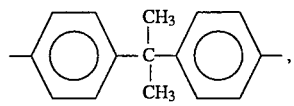

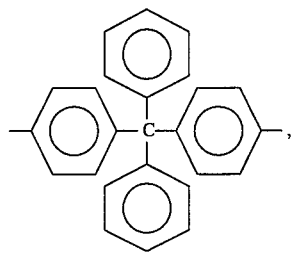

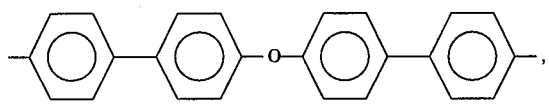

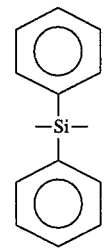

In the general formula (I), $L^1$ to $L^4$ indicate each independently a substituted or unsubstituted ligand having one of the formulae:

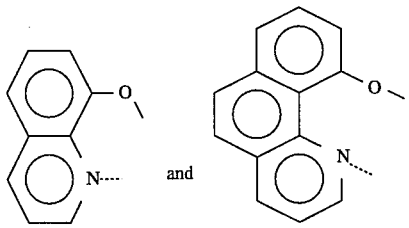 and 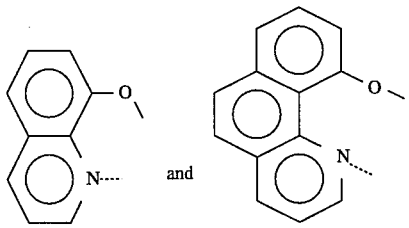

Examples of the substituent are alkyl groups having 1 to 6 carbon atoms, such as methyl group, ethyl group, propyl group, isopropyl group, n-butyl group, isobutyl group, tert-butyl group, sec-butyl group, isopentyl group, tert-pentyl group, neopentyl group, hexyl group, isohexyl group and the like, alkoxy groups having 1 to 6 carbon atoms corresponding to the alkyl groups, phenyl group, cyclohexyl group, cyano group, halogen atoms (chlorine atom, fluorine atom and bromine atom), nitro group and the like.

It is preferable that $L^1$ to $L^4$ are each 2-methylquinolyl-8-oxy group having the formula:

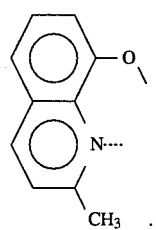
Specific examples of the compound having an aluminum complex structure represented by the general formula (I) used in the present invention are:
(Chemical Formula 1)
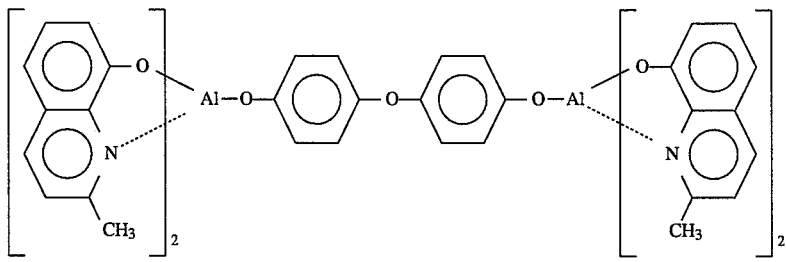
(Chemical Formula 2)
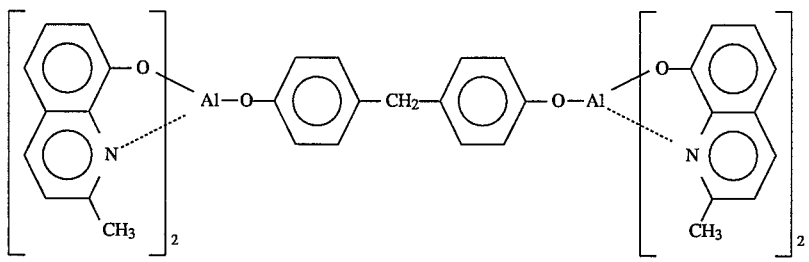
(Chemical Formula 3)
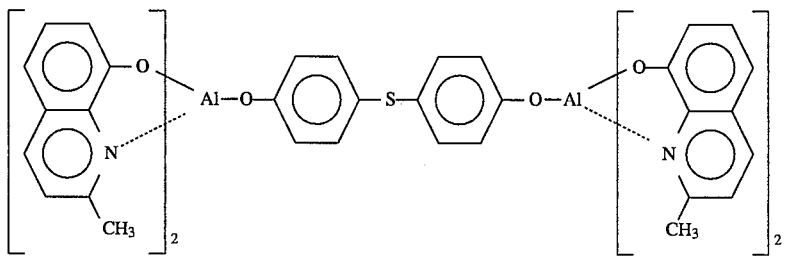
(Chemical Formula 4)
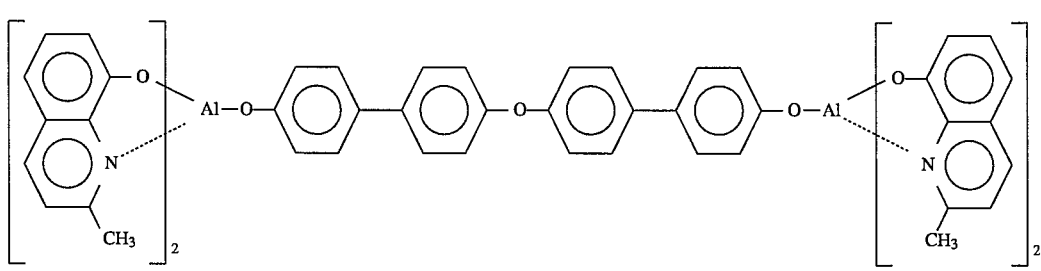

-continued
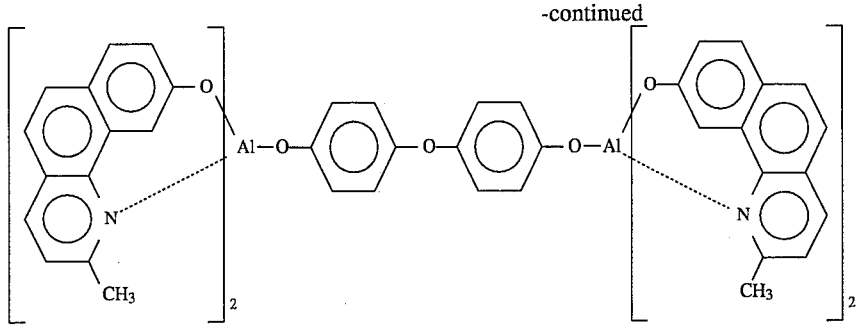
(Chemical Formula 5)
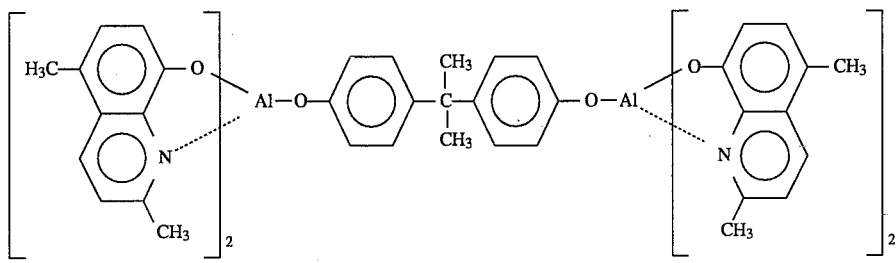
(Chemical Formula 6)
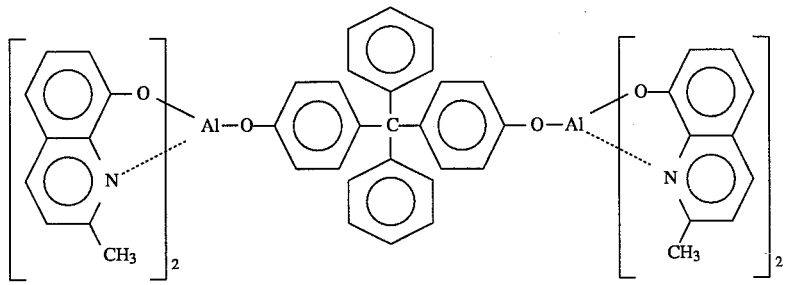
(Chemical Formula 7)
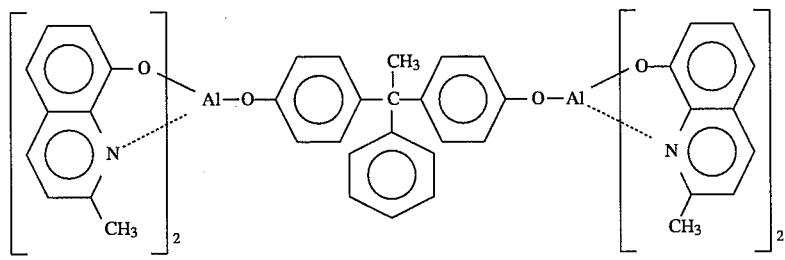
(Chemical Formula 8)
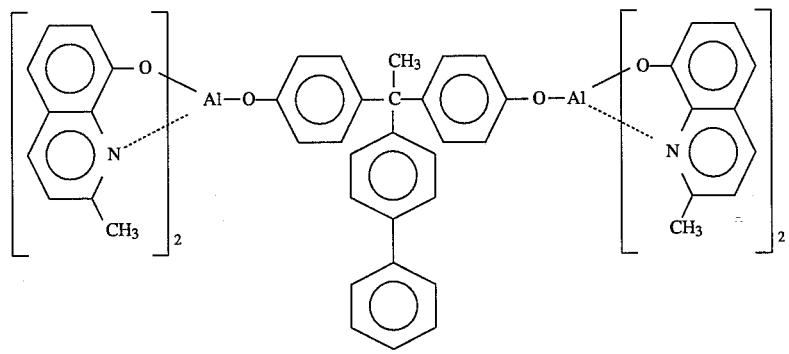
(Chemical Formula 9)

-continued
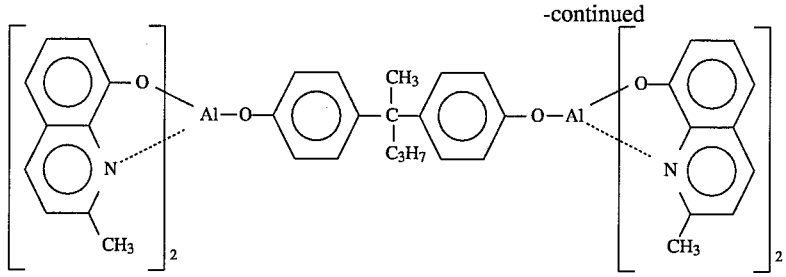
(Chemical Formula 10)
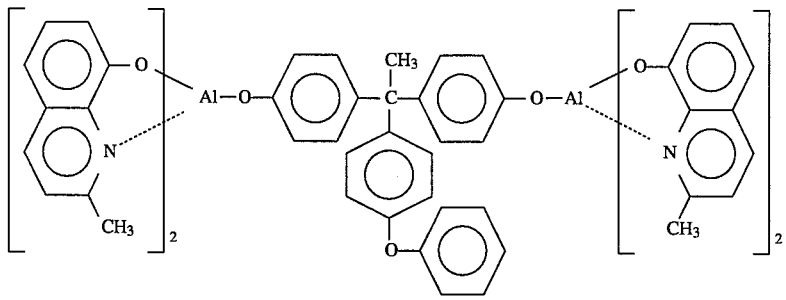
(Chemical Formula 11)
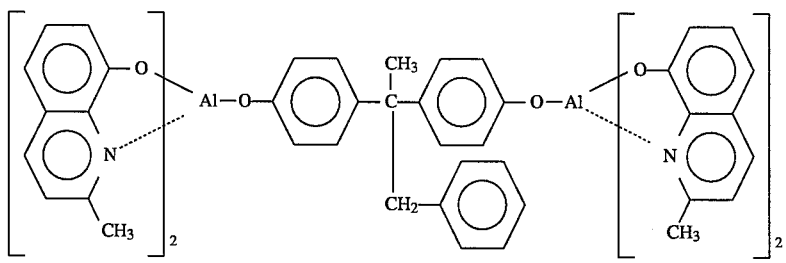
(Chemical Formula 12)
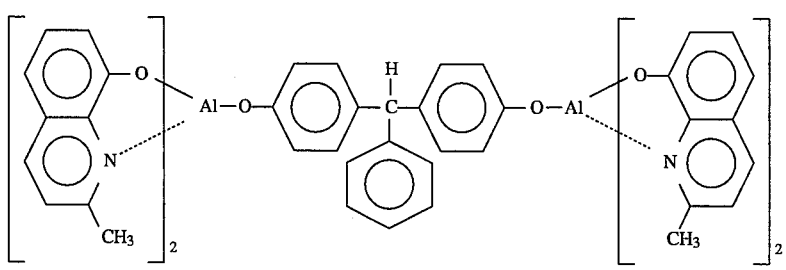
(Chemical Formula 13)
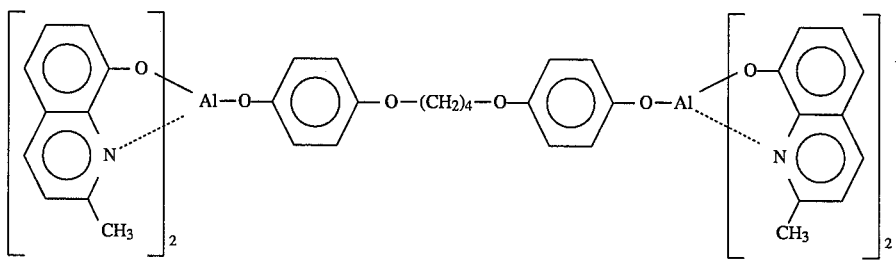
(Chemical Formula 14)
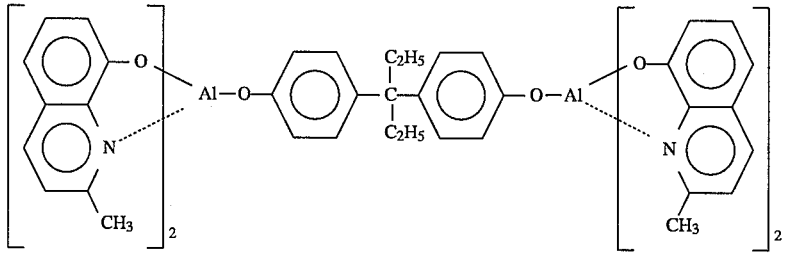
(Chemical Formula 15)

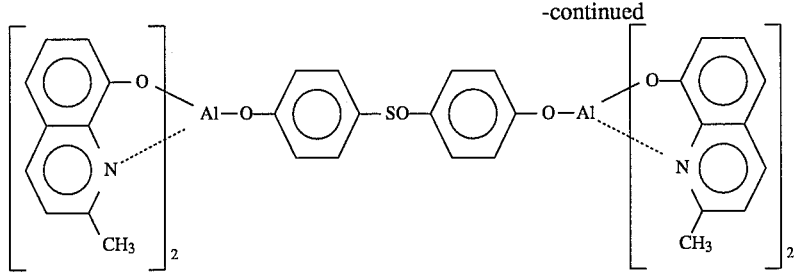
(Chemical Formula 16)
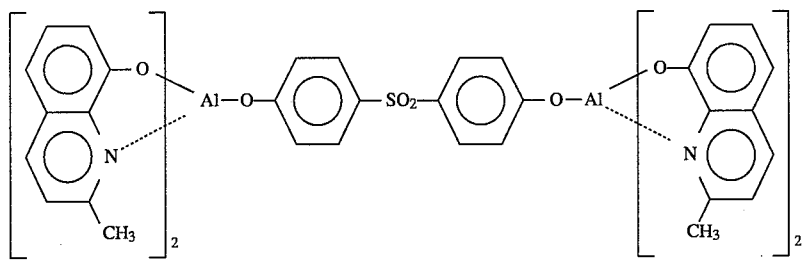
(Chemical Formula 17)
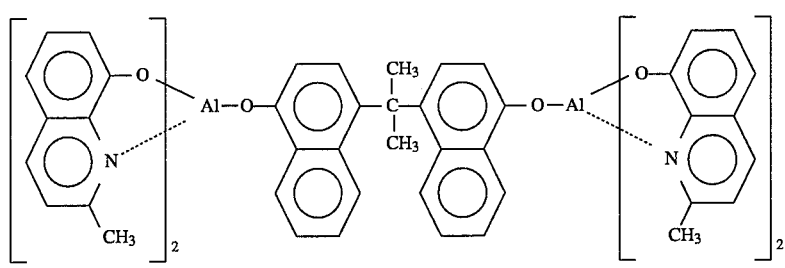
(Chemical Formula 18)
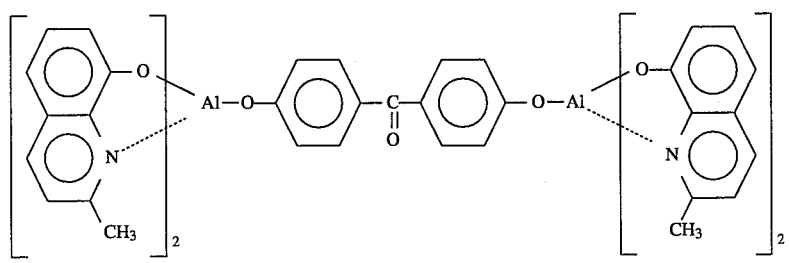
(Chemical Formula 19)
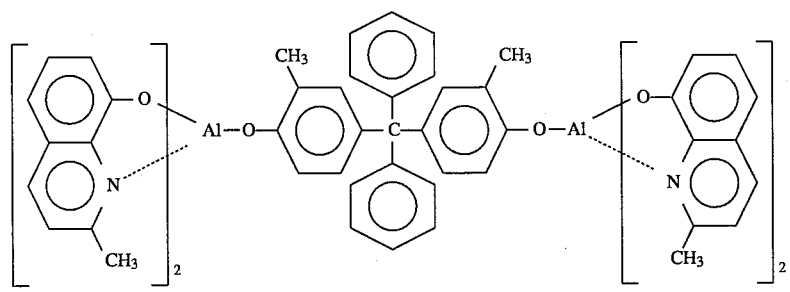
(Chemical Formula 20)
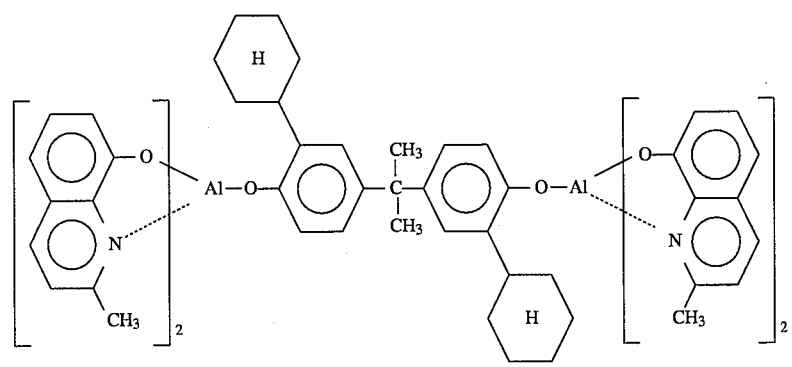
(Chemical Formula 21)

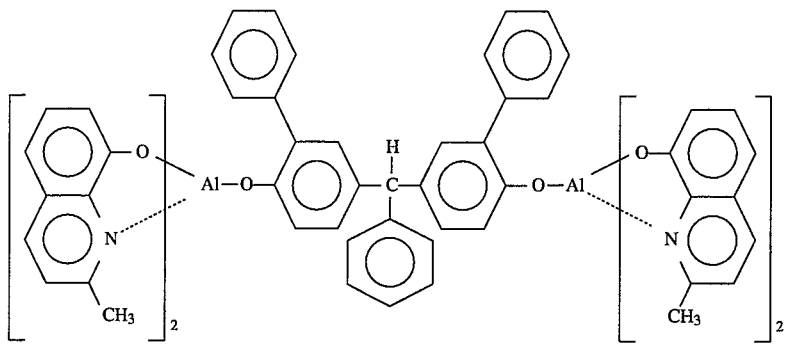
(Chemical Formula 22)
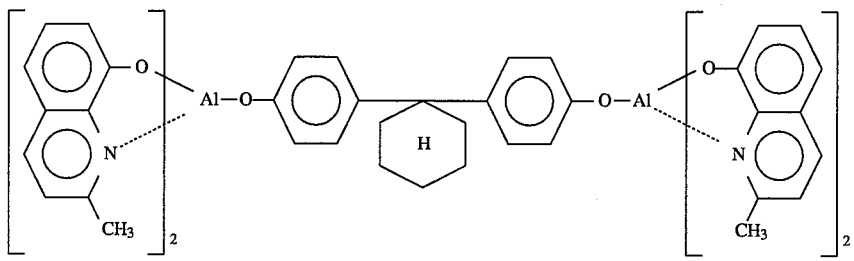
(Chemical Formula 23)
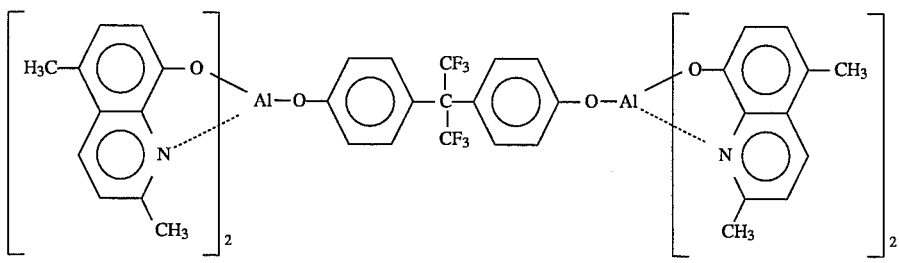
(Chemical Formula 24)
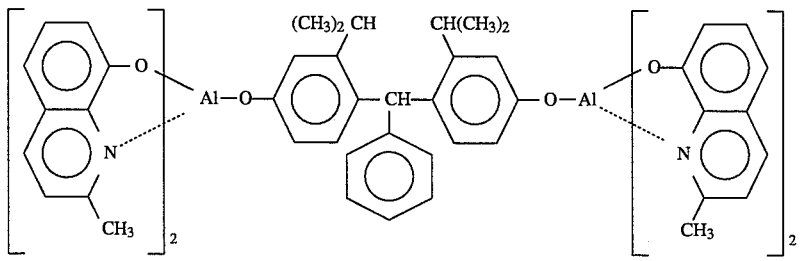
(Chemical Formula 25)
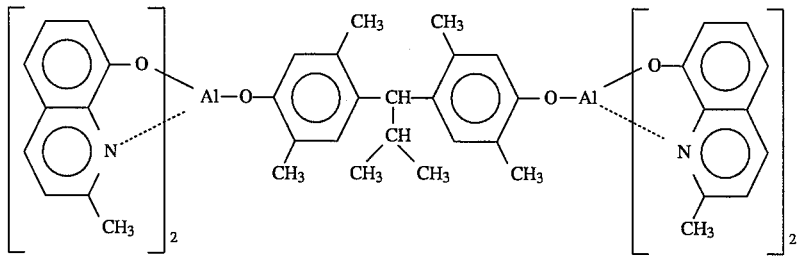
(Chemical Formula 26)
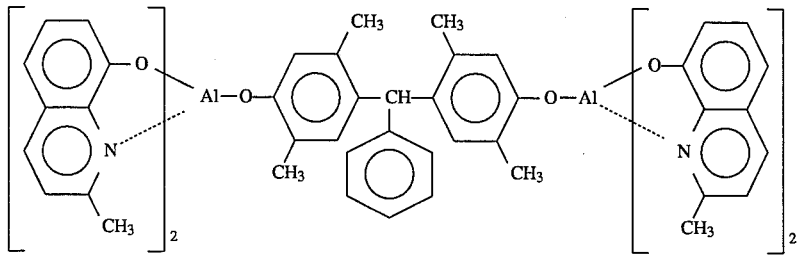
(Chemical Formula 27)

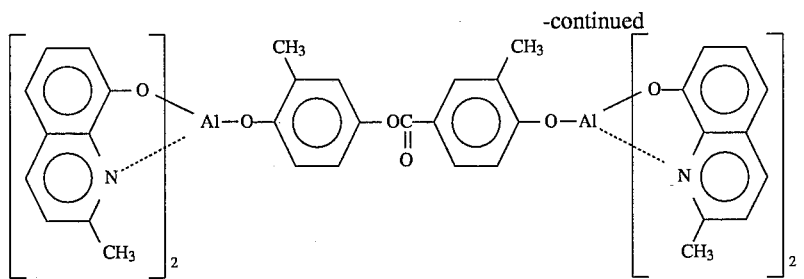
(Chemical Formula 28)

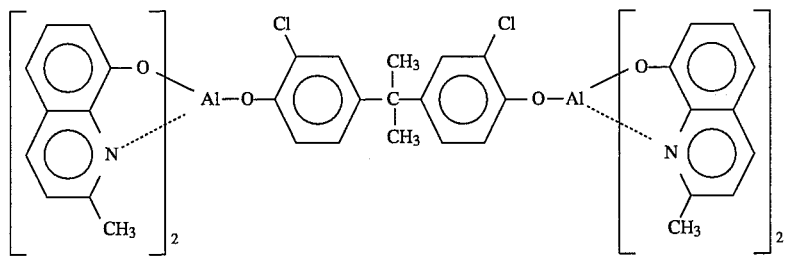
(Chemical Formula 29)

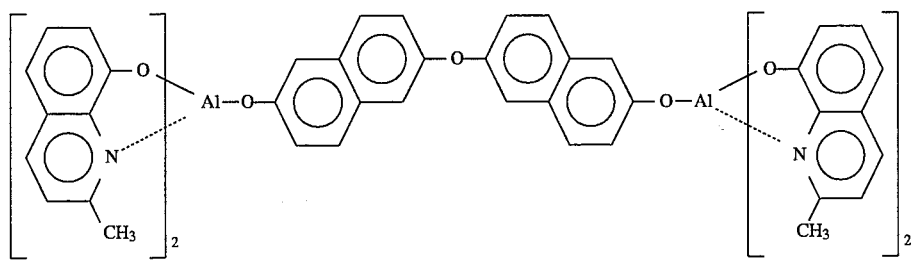
(Chemical Formula 30)

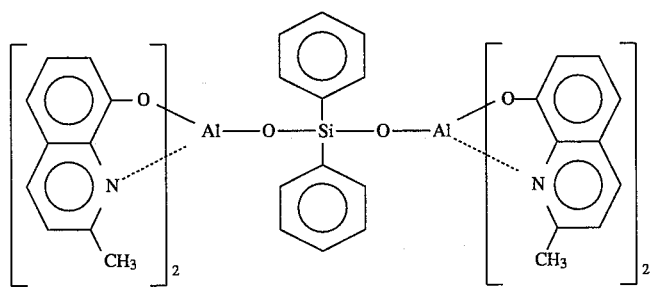
(Chemical Formula 31)

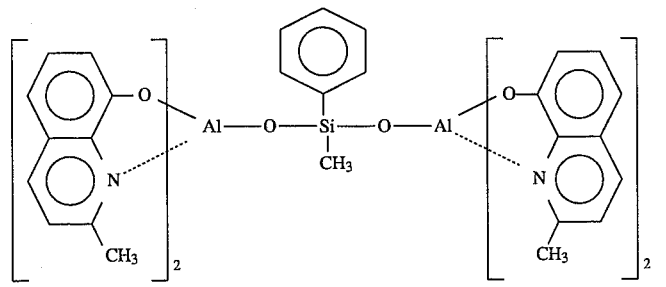
(Chemical Formula 32)

The compound having an aluminum complex structure of the present invention contains an aromatic ring or a substituted silylene group in the compound as shown in the above examples. Particularly, exhibition of various characteristics which cannot be obtained by low molecular weight compounds is enabled by the dimerized structure of the aluminum complex.

More specifically, melting point is increased by increase in the molecular weight to prevent melting or crystallization of the compound by the heat generated in the device. Crystallization is also suppressed by the steric effect of the molecule. Thus, improvement of the property to form a thin film is enabled.

The present invention relates to the organic EL device comprising the compound having an aluminum complex structure represented by the general formula (I) described above. The device has, for example, a structure of anode/hole injecting and transporting layer/light emitting layer/electron injecting and transporting layer/cathode; a structure of anode/light emitting layer/electron injecting and transporting layer/cathode; a structure of anode/hole injecting and transporting layer/light emitting layer/cathode; a structure of anode/light emitting layer/cathode or the like structure. The compound having an aluminum complex structure represented by the general formula (I) described above preferably forms the light emitting layer and/or the electron injecting and transporting layer. The hole injecting and transporting layer and the electron injecting and transporting layer are not necessarily comprised in the structure of the organic EL device of the present invention. However, the organic EL device comprising these layers has an advantage that the light emitting property is enhanced. The hole injecting and transporting layer, the light emitting layer and the electron injecting and transporting layer described above may be placed between a pair of electrodes in a mixed form, as well. Furthermore, a mixed layer may be formed using a binder of a macromolecular compound or the like additionally to distribute the components in a stabilized form.

The organic EL device of the present invention is described in the following using a device having the structure of anode/hole injection and transporting layer/light emitting layer/electron injecting and transporting layer/cathode as an example.

The device of the present invention is preferably supported on a substrate. The substrate is not particularly limited but a substrate used in conventional organic EL devices, such as glass, transparent plastic, quartz or the like, can be used.

As an electrode material of the anode in the organic EL device of the present invention, a metal, an alloy, an electric conductive compound or a mixture thereof, all having a large work function (4 eV or more), is preferably used. Specific examples of the electrode material are metals, such as Au, and transparent materials having electric conductivity, such as CuI, ITO, $SnO_2$, ZnO and the like. The anode can be prepared by forming the electrode material into a thin film by the vapor deposition method or the sputtering method. To obtain light emission from the electrode, it is preferable that light transmittance of the electrode is more than 10% and resistance of the sheet as the electrode is preferably several hundred $\Omega/\square$ or less.

Film thickness of the anode is in the range of 10 nm to 1 μm, preferably in the range of 10 to 200 nm, although it is varied depending on the kind of the material.

On the other hand, as an electrode material of the cathode, a metal, an alloy, an electric conductive compound or a mixture thereof, all having a small work function (4 eV or less), is preferably used. Specific examples of the electrode material are sodium, sodium-potassium alloy, magnesium, lithium, magnesium/copper mixtures, magnesium/silver mixtures, $Al/Al_2O_3$, indium and the like. The anode can be prepared by forming the electrode material into a thin film by the vapor deposition method or the sputtering method. Resistance of the sheet as the electrode is preferably several hundred $\Omega/\square$ or less. Film thickness is usually in the range of 10 to 500 nm, preferably in the range of 50 to 200 nm. It is advantageous that either the anode or the cathode in the organic EL device is transparent or translucent because the emitted light is transmitted more easily through the electrode and obtained with a higher efficiency.

As the light emitting material of the light emitting layer of the present invention, the compound having an aluminum complex structure represented by the general formula (I) described above is preferable. When the compound having an aluminum complex structure is used in a layer other than the light emitting layer, the material of the light emitting layer is not particularly limited but selected for use from generally known materials according to desire.

As the light emitting material other than the compound having an aluminum complex structure, compounds having suitable property to form a thin film, such as polycyclic condensed aromatic compounds, fluorescence whitening agents like benzoxazole agents, benzothiazole agents, benzimidazole agents and the like, metal chelated oxanoid compounds, distyrylbenzene compounds and the like, can be used. Examples of the polycyclic condensed aromatic compound are condensed ring light emitting compounds containing a skeleton of anthrathene, naphthalene, phenanthrene, pyrene, chrysene, perylene or the like.

As the fluorescence whitening agent like benzoxazole agents, benzothiazole agents, benzimidazole agents or the like described above, for example, compounds described in Japanese Patent Application Laid-Open No. 194393/1984 can be used. Representative examples are: benzoxazole compounds, such as 2,5-bis-(5,7-di-t-pentyl-2-benzoxazolyl)- 1,3,4-thiadiazole, 4,4'-bis(5,7-t-pentyl-2-benzoxazolyl)stilbene, 4,4'-bis(5,7 -di-(2-methyl-2-butyl)-2-benzoxazolyl)stilbene, 2,5-bis(5,7-di-t-pentyl-2-benzoxazolyl)thiophene, 2,5-bis(5-(α,α-dimethylbenzyl)-2-benzoxazolyl)thiophene, 2,5-bis(5,7-di-(2-methyl-2-butyl)-2-benzoxazolyl)-3,4-diphenylthiophene, 2,5-bis(5-methyl-2-benzoxazolyl)thiophene, 4,4'-bis(2-benzoxazolyl)biphenyl, 5-methyl-2-(2-(4-(5-methyl-2-benzoxazolyl)phenyl)vinyl)benzoxazole, 2-(2-(4-chlorophenyl)vinyl)naphtho(1,2-d)oxazole and the like; benzothiazole compounds, such as 2,2'-(p-phenylenedivinylene)-bis-benzothiazole and the like; benzimidazole compounds, such as 2-(2-(4-( 2-benzimidazolyl)phenyl)vinyl)benzimidazole, 2-(2-(4-carboxyphenyl)vinyl)benzimidazole and the like; and the like fluorescence whitening agents. Still other examples of the useful compounds are those described in Chemistry of Synthetic Dyes, Pages 628 to 637 and 640, 1971.

As the metal chelated oxanoid compound described above, for example, compounds described in Japanese Patent Application Laid-Open No. 295695/1988 can be used. Representative examples are 8-hydroxyquinoline metal complexes, such as tris(8-quinolinol) aluminum, bis(8-quinolinol) magnesium, bis(benzo(f)-8-quinolinol) zinc, bis(2-methyl-8-quinolinolato) aluminum oxide, tris((8-quinolinol) indium, tris(5-methyl-8-quinolinol) aluminum, 8-quinolinol lithium, tris(5-chloro-8-quinolinol) gallium, bis(5-chloro-8-quinolinol) calcium, poly(zinc(II)-bis(8-hydroxy-5-quinolinonyl)methane and the like; dilithium epindridion; and the like.

Metal chelated oxanoid compounds doped with a polycyclic aromatic compound which are described in U.S. Pat. Nos. 5,141,671 (1992) and 5,150,006 (1992) can be used, as well. Specific examples of these compounds are 8-hydroxyquinoline metal chelated complexes, such as bis(2-methyl-8-quinolinolato) (phenolato) aluminum (III), bis(2-methyl-8-quinolinolato)(cresolato) aluminum (III), bis(2 -methyl-8-quinolinolato) (phenylphenolato) aluminum (III), bis(2-methyl- 8-quinolinolato) (naphtholato) aluminum (III), bis(2-methyl-8-quinolinolato)aluminum (III) -μ-oxo-bis(2-methyl-8-quinolinolato)aluminum (III) and the like, which are doped with a polycyclic aromatic compounds, such as perylene, dibenzoperylene or the like.

Still other examples are distyrylbenzene derivatives described in the specification of European Patent No. 0373582, dimethylidene derivatives described in the specification of European Patent No. 0388768, coumarine derivatives described in Japanese Patent Application Laid-Open No. 191694/1990, distyrylpyrazine derivatives described in Japanese Patent Application Laid-Open No. 252793/1990, perylene derivatives described in Japanese Patent Application Laid-Open No. 196885/1990, naphthalene derivatives described in Japanese Patent Application Laid-Open No. 255789/1990, phthaloperynone derivatives described in Japanese Patent Application Laid-Open Nos. 289676/1990 and 88689/1990, styrylamine derivatives described in Japanese Patent Application Laid-Open No. 250292/1990, cyclopentadiene derivatives described in Japanese Patent Application Laid-Open No. 289675/1990, polyphenyl compounds described in the specification of European Patent 387715, and the like. A compound can be selected for use suitably according to the desired color of emitted light and other desired properties.

The light emitting layer containing the organic compound described above may have a laminated structure containing two or more layers according to desire. It may also be formed with addition of a fluorescent substance or a polycyclic aromatic compound as disclosed in the specifications of U.S. Pat. Nos. 4,769,292 and 5,141,671. In this case, the organic compound described above forms a layer of thin film and has a part of the injection function and a part of the light emitting function in the functions of the light emitting region. On the other hand, the fluorescent substance is present in the layer of the organic compound in a small amount (several mol % or less) and has a part of the light emitting function which leads to emission of light in response with recombination of an electron and a hole.

The light emitting layer may consist of one layer comprising one or more of the light emitting materials, or may be a laminate with a light emitting layer comprising other compounds than the materials for the light emitting layer described above.

Next, the hole injecting and transporting layer in the organic EL device of the present invention comprises a hole transfer compound and has the function of transferring holes injected from the anode to the light emitting layer. By the presence of this hole injecting and transporting layer between the anode and the light emitting layer, a larger amount of hole is injected into the light emitting layer with a lower electric field. Furthermore, electrons injected into the light emitting layer from the cathode or the electron injecting and transporting layer are accumulated at the interface in the light emitting layer because of an electron barrier existing at the interface of the light emitting layer and the hole injecting and transporting layer and the efficiency of light emission is enhanced. Thus, a device having excellent light emitting property can be obtained by the presence of the hole injecting and transporting layer.

The hole transferring compound used in the hole injecting and transporting layer is placed between the two electrodes loaded with an electric field and can transfer holes to the light emitting layer in an appropriate manner when the holes are injected from the anode. For example, a compound having mobility of holes of at least $10^{-6} cm^2/V.sec$ in an electric field of $10^4$ to $10^6$ V/cm is preferably used.

The hole transferring compound is not particularly limited so long as it has the favorable property described above. A compound can be selected for use from conventional materials used as charge injecting and transporting materials of holes in photo-conductive materials and generally known materials used as hole injecting and transporting layers in EL devices according to desire.

Examples of the hole transferring compound are: triazole derivatives (described in the specification of U.S. Pat. No. 3,112,197, etc.), oxadiazole derivatives (described in the specification of U.S. Pat. No. 3,189,447, etc.), imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, and the like.

Examples of the charge injecting and transporting material are silazane derivatives, polysilane-based materials, aniline-based copolymers, electric conductive polymeric oligomers, particularly thiophene oligomers, and the like.

In the present invention, the above hole transferring compound or the above charge injecting and transporting material can be used as the hole injecting material. However, porphyrin compounds (described in Japanese Patent Application Laid-Open No. 295695/1988, etc.) and aromatic tertiary amine compounds and styrylamine compounds (described in the specification of U.S. Pat. No. 4,127,412; in Japanese Patent Application Laid-Open Nos. 27033/1978, 58445/1979, 149634/1979, 64299/1979, 79450/1980, 144250/1980, 119132/1981, 295558/1986, 98353/1986 and 295695/1988, etc.) shown in the following are preferably used. Particularly preferably, said aromatic tertiary amine compounds are used.

Representative examples of the porphyrin compound are: porphin, 5,10,15,20-tetraphenyl-21H,23H-porphin copper (II), 5,10,15,20 -tetraphenyl-21H,23H-porphin zinc (II), 5,10,15,20-tetrakis(pentafluorophenyl)- 21H,23H-porphin, silicon phthalocyanine oxide, aluminum phthalocyanine chloride, phthalocyanine (no metal), dilithium phthalocyanine, copper tetramethylphthalocyanine, copper phthalocyanine, chromium phthalocyanine, zinc phthalocyanine, lead phthalocyanine, titanium phthalocyanine oxide, magnesium phthalocyanine, copper octamethylphthalocyanine and the like.

Representative examples of the aromatic tertiary amine compound and the styrylamine compound are: N,N,N',N'-tetraphenyl-4,4'-diaminobiphenyl, N,N'-diphenyl-N,N'-di(3-methylphenyl)-4,4'-diaminobiphenyl (TPDA), 2,2-bis(4-di-p-tolylaminophenyl)propane, 1,1-bis(4-di-p-tolylaminophenyl)cyclohexane, N,N,N',N'-tetra-p-tolyl-4, 4'-diaminobiphenyl, 1,1-bis(4-di-p-tolylaminophenyl)-4-phenylcyclohexane, bis(4 -dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenyl ether, 4,4'-bis(diphenylamino)terphenyl, N,N,N-tri(p-tolyl)amine, 4,4'-bis[4-(di-p-tolylamino)stilbene], 4-N,N-diphenylamino-(2, 2-diphenylvinyl)benzene, 3-methoxy-4'-N,N-diphenylaminostilbene, N-phenylcarbazole, and the like.

The hole injecting and transporting layer may consist of one layer comprising one or more of these hole injecting and transporting materials, or may be a laminate with a hole injecting layer comprising other compounds than the materials for the hole injecting layer described above.

The electron injecting and transporting layer in the organic EL device of the present invention comprises an electron injecting and transporting material and has the function of transferring electrons injected from the cathode to the light emitting layer. The compounds represented by the general formula (I) described above are preferably used in the present invention. When the compound having an aluminum complex structure is used in a layer other than the electron injecting and transporting layer, the electron injecting material is not particularly limited, but a compound is selected for use from conventional materials according to desire.

The electron injecting and transporting layer may consist of one layer comprising one or more of these electron injecting materials, or may be a laminate with an electron injecting and transporting layer comprising other compounds than the electron injecting and transporting materials described above.

Furthermore, inorganic hole injecting and transporting materials comprising p-type α-Si, N-type α-SiC or the like and inorganic electron injecting and transporting materials comprising n-type α-Si, n-type α-SiC or the like can also be used as the electron injecting and transporting material of the present invention. For example, inorganic semiconducting materials disclosed in International Patent Application Laid-Open No. WO 90/05998 can be used.

Next, the method of preparation of the organic EL device of the present invention is described with a preferable example. The method of preparation of the EL device composed of anode/hole injecting and transporting layer/light emitting layer/electron injecting and transporting layer/cathode which is mentioned above is described as such a preferable example. A thin film made of a desired electrode material, for example an anode material, is formed to a thickness of 1 μm or less, preferably in the range of 10 to 200 nm by a method, such as the vapor deposition method, the sputtering method or the like, as the anode. Then, thin films made of materials of the device, such as materials of the hole injection and transporting layer, the light emitting layer and the electron injecting and transporting layer, are formed on the anode.

As the method of forming a thin film, the spin coating method, the casting method, the vacuum vapor deposition method or the like can be used as described above. The vacuum vapor deposition method is preferable among them because a uniform thin film is more easily obtained and possibility of formation of pin-holes is smaller. When the vacuum vapor deposition method is adopted for the formation of a thin film, conditions of the vacuum vapor deposition are different according to the kind of compound used, the crystal structure to be formed in the molecular accumulated film, the structure of aggregation, and the like. It is generally preferred that the conditions are suitably selected in the ranges of 50° to 400° C. for the heating temperature of a boat, $10^{-6}$ to $10^{-3}$ Pa for the vacuum, 0.01 to 50 nm/sec for the rate of vapor deposition, −50° to 300° C. for the substrate temperature and 5 nm to 5 μm for the film thickness.

After these layers are formed, a thin film made of a cathode material is formed to a thickness of 1 μm or less, preferably 50 to 200 nm, by a method, such as the vapor deposition method or the sputtering method, to form the cathode. Thus, the desired EL device can be obtained. In the preparation of the EL device, it is possible that order of the preparation is reversed and the layers are prepared in the order of the cathode, the electron injecting and transporting layer, the light emitting layer, the hole injection and transporting layer and the anode.

When the device has the structure of anode/light emitting layer/cathode in which the hole injecting and transporting layer, the light emitting layer and the electron injecting and transporting layer are placed in a mixed form between a pair of electrode, for example, a thin film made of the anode material is formed on a suitable substrate as the first step of preparation of the device. Then, the light emitting layer is formed on this film by coating a solution containing the hole injecting and transporting material, the light emitting material, the electron injecting and transporting material, a binder, such as polyvinylcarbozole, polycarbonate, polyarylate, polyester, polyether or the like, and the like materials or by dip coating of this solution. A thin film made of the cathode material is formed on the light emitting layer thus formed. A device material which is a material of the light emitting layer or the electron injecting and transporting layer may be coated on the light emitting layer prepared above by the vapor deposition method before a thin film made of the cathode material is formed on it.

When the EL device thus prepared is loaded with a direct voltage, light emission is observed with a voltage of 3 to 40 V in the condition that the anode is connected to a positive electrode (+) and the cathode is connected to a negative electrode (−). When the connection is reversed, no electric current is observed and no light is emitted at all. When the EL device is loaded with an alternating voltage, light emission is observed only in the condition that the polarity of the anode is positive and the polarity of the cathode is negative. Wave shape of the loaded alternating voltage is selected according to desire.

A method of synthesis of the compound having an aluminum complex structure represented by the general formula (I) which is the characteristic compound of the present invention is briefly described in the following with a 8-hydroxyquinoline derivative as an example. However, the method of synthesis of the compound having an aluminum complex structure used in the present invention is not limited to the method described in the following.

The compound having an aluminum complex structure represented by the general formula (I) can be synthesized according to the method shown in the following scheme of synthesis:

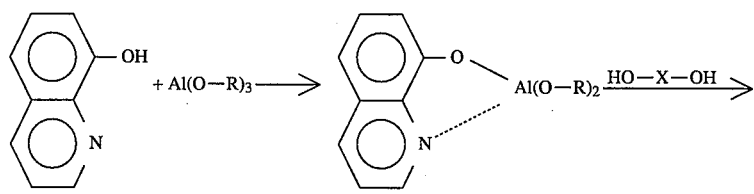

-continued

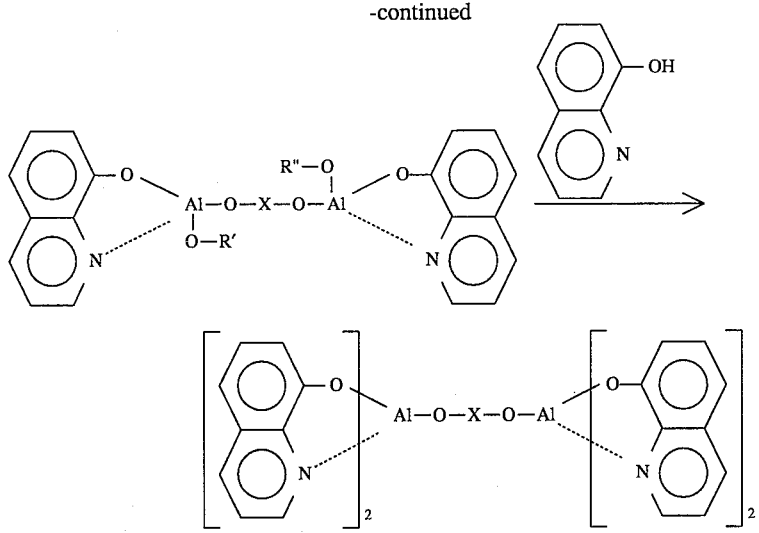

wherein R, R' and R" are each an alkyl group and X is the same as that described above.

More specifically, 1 equivalent each of a 8-hydroxyquinoline derivative (referred to as Hhg; 8-hydroxyquinoline is used as an example in the scheme shown above.) and an aluminum alkoxide are heated for about 1 hour under stirring in a solvent, such as an alcohol (methanol, ethanol, propanol, butanol, amyl alcohol or the like), benzene, toluene or the like. After cooling by standing, ½ equivalent of a dihydroxy compound is added and stirred. Then, 1 equivalent of Hhg is further added and stirred. The reaction time is preferably 3 to 20 hours. Amounts of by-products are sometimes decreased when, after the dihydroxy compound is added, the solution is heated for about 1 hour under stirring and cooled by standing and, then, the additional amount of Hhg is added. When the kind of Hhg added first and the kind of Hhg added next are different, a complex of aluminum with different kinds of Hhg can be obtained.

Examples of Hhg used here are 8-hydroxyquinoline, 2-methyl-8-hydroxyquinoline, 5-methyl-8-hydroxyquinoline, 7-nitro-8-hydroxyquinoline, 5-nitro-8-hydroxyquinoline, 5-chloro-8-hydroxyquinoline, 5-fluoro-8-hydroxyquinoline and the like. 10-Hydroxybenzo(h)quinoline and the like are also included in the 8-hydroxyqunoline derivatives.

Examples of the aluminum alkoxide are aluminum isopropoxide, aluminum t-butoxide, aluminum ethoxide and the like.

Examples of the dihydroxy compound are 4,4'-dihydroxybiphenyl ether, 3,3'-dihydroxybiphenyl ether, 3,4'-dihydroxybiphenyl ether, 4,4'-dihydroxybiphenyl thioether, 4,4'-dihydroxybiphenylmethane, 1,1-bis(4-hydroxyphenyl)ethane, 1,2-bis(4-hydroxyphenyl)ethane, 2,2-bis(4-hydroxyphenyl)propane, 2,2-bis(4-hydroxyphenyl)butane, 2,2-bis(3-methyl-4-hydroxyphenyl)butane, 1,1-bis(4-hydroxyphenyl)-1,1-diphenylmethane, 1,1-bis(4-hydroxyphenyl)-1-phenylethane, 1,1-bis(4-hydroxyphenyl) sulfide, 1,1-bis(4-hydroxyphenyl) sulfone, 1,1-bis(4-hydroxyphenyl) ketone, 1,1-bis(4-hydroxyphenyl)cyclohexane, 1,1'-oxybis(4-hydroxybiphenyl), diphenylsilanediol, and the like.

The compound having an aluminum complex structure represented by the general formula (I) of the present invention can be used not only as the component of the organic EL device but also as a coating material of optical materials, a fluorescence material, an electronic material, a waveguide material, a plastic scintillator, an organic scintillator, a core or clad material in fibers, a polymerization catalyst, a pigment, an additive for ink or the like.

The organic EL device of the present invention uses the novel compound having an aluminum complex structure as the component thereof. The constituting layers in the organic EL device have excellent adhesion with the electrodes. The organic EL device has excellent properties of high luminance, high efficiency of light emission and long life time and is advantageously used as a light emitting device in various kinds of display apparatus.

The compound having an aluminum complex structure of the present invention not only provides the device with above-mentioned excellent properties when it is used as a component of the device but also is advantageously used as a coating material of optical materials, an electronic material, a waveguide material, a scintillator or the like.

The present invention is described in more detail with reference to examples in the following; however, these examples are intended to illustrate the invention and are not to be construed to limit the scope of the invention.

SYNTHESIS EXAMPLE 1 (CHEMICAL FORMULA 1)

Synthesis of bis(2-methyl-8-quinolinato) aluminum (III)-µ-4,4'-oxybis(4-phenoxy)-bis(2-methyl-8-quinolinato) aluminum (III)

2-Methyl-8-hydroxyquinoline (Hmhq, a product of Tokyo Kasei Co., Ltd.) in an amount of 1.6 g (0.01 mol) and aluminum isopropoxide (a product of Tokyo Kasei Co., Ltd.) in an amount of 2.0 g (0.01 mol) were added to 80 milliliter of ethanol. The mixture was heated for 30 minutes under stirring and cooled by standing.

Then, 5 g of sodium sulfate was added to the solution obtained and the mixture was stirred and filtered. To the filtrate solution thus obtained, 1.0 g (0.005 mol) of 4,4'-dihydroxybiphenyl ether was added and stirred. Then, 1.6 g (0.01 mol) of Hmhq was added. The mixture was heated under stirring and kept refluxing for 5 hours in an oil bath under an argon stream. After cooling the mixture by standing, powder precipitated out was separated by filtration with a reduced pressure, washed with 10 milliliter of ethanol and dried to obtain 2.0 g (0.00225 mol) of a light yellow powder.

Yield of the object product was 45%.

As the result of mass spectrometric analysis of the light yellow powder obtained, the following value was obtained: m/Z=886 (M$^+$).

As the result of measurement of proton nuclear magnetic resonance ($^1$H-NMR; reference, tetramethylsilane (TMS); solvent, dimethylsulfoxide (DMSO); wave length of the measurement, 400 MHz), the following values were obtained:

δ=2.6~3.2 ppm (s, 12H, H of the methyl group at the quinoline ring)

δ=6.1~8.3 ppm (m, 28H, H of the quinoline ring and the phenyl ring)

It was found from the above result that ratio of H of the saturated parts and H of the unsaturated parts was 3:7.

In Examples described below, the light yellow powder was used after purification by sublimation.

SYNTHESIS EXAMPLE 2 (CHEMICAL FORMULA 2)

Synthesis of bis(2-methyl-8-quinolinato) aluminum (III)-μ-4,4'-dioxydiphenylmethylene-bis( 2-methyl-8-quinolinato) aluminum (III)

The above compound was synthesized by the same method as that in Synthesis Example 1 except that 0.005 mol of 4,4'-dihydroxydiphenylmethane was used in place of 4,4'-dihydroxybiphenyl ether.

As the result of the synthesis, 4.3 g (0.0048 mol) of a light yellow powder was obtained.

Yield of the object product was 96%.

As the result of mass spectrometric analysis of the light yellow powder obtained, the following value was obtained: m/Z=884 (M$^+$).

As the result of measurement of proton nuclear magnetic resonance ($^1$H-NMR; reference, tetramethylsilane (TMS); solvent, dimethylsulfoxide (DMSO); wave length of the measurement, 400 MHz), the following values were obtained:

δ=3.0 ppm (s, 12H, H of the methyl group at the quinoline ting)

δ=2.65 ppm (s, 2H, H of the central methylene)

δ=6.15~8.25ppm (m, 28H, H of the quinoline ring and the phenyl ring)

It was found from the above result that ratio of H of the saturated parts and H of the unsaturated parts is 14:28.

As the result of elemental analysis, the following values were obtained (values in the parentheses are theoretical values): C: 71.72 (72.33) %; H: 4.63 (4.78) %; N: 6.43 (6.32) %.

In Examples described below, the light yellow powder was used after purification by sublimation.

SYNTHESIS EXAMPLE 3 (CHEMICAL FORMULA 4)

Synthesis of bis(2-methyl-8-quinolinato) aluminum (III)-μ-1,1'-oxybis( 4'-oxy-p-phenylphenylene)-bis(2-methyl-8-quinolinato) aluminum (III)

The above compound was synthesized by the same method as that in Synthesis Example 1 except that 0.005 mol of 1,1'-oxybis(4-hydroxybiphenyl) was used in place of 4,4'-dihydroxybiphenyl ether.

As the result of the synthesis, 4.2 g (0.0040 mol) of a white powder was obtained.

Yield of the object product was 81%.

As the result of mass spectrometric analysis of the white powder obtained, the following value was obtained: m/Z= 1038 (M$^+$).

As the result of elemental analysis, the following values were obtained (values in the parentheses are theoretical values): C: 73.80 (73.98) %; H: 4.57 (4.62) %; N: 5.40 (5.39) %.

In Examples described below, the white powder was used after purification by sublimation.

SYNTHESIS EXAMPLE 4 (CHEMICAL FORMULA 6)

Synthesis of bis(2-methyl-8-quinolinato) aluminum (III)-μ-2,2bis( 4-oxyphenyl)propylene-bis(2-methyl-8-quinolinato) aluminum (III)

The above compound was synthesized by the same method as that in Synthesis Example 1 except that 0.005 mol of 2,2-bis(4-hydroxyphenyl)propane was used in place of 4,4'-dihydroxybiphenyl ether.

After cooling the reaction mixture by standing, powder precipitated out was removed by filtration with a reduced pressure. The filtrate solution thus obtained was concentrated to about 20 milliliter. Light yellow powder precipitated out was separated by filtration with a reduced pressure, washed with a small amount of methanol and then dried to obtain 1.2 g (0.0013 mol) of light yellow powder.

Yield of the object product was 26%.

As the result of mass spectrometric analysis of the light yellow powder obtained, the following value was obtained: m/Z=912 (M$^+$).

As the result of elemental analysis, the following values were obtained (values in the parentheses are theoretical values): C: 84.38 (84.29) %; H: 5.36 (5.26) %; N: 6.06 (6.14) %.

In Examples described below, the light yellow powder was used after purification by sublimation.

SYNTHESIS EXAMPLE 5 (CHEMICAL FORMULA 7)

Synthesis of bis(2-methyl-8-quinolinato) aluminum (III)-μ-1,1-bis( 4-oxyphenyl)-1,1-diphenylmethylene-bis(2-methyl-8- quinolinato) aluminum (III)

The above compound was synthesized by the same method as that in Synthesis Example 1 except that 0.005 mol of 1,1-bis(4-hydroxyphenyl)- 1,1-diphenylmethane was used in place of 4,4'-dihydroxybiphenyl ether.

As the result of the synthesis, 1.76 g (0.0017 mol) of light yellow powder was obtained.

Yield of the object product was 34%.

As the result of mass spectrometric analysis of the light yellow powder obtained, the following value was obtained: m/Z=1036 (M$^+$).

As the result of measurement of proton nuclear magnetic resonance ($^1$H-NMR; reference, tetramethylsilane (TMS);

solvent, dimethylsulfoxide (DMSO); wave length of the measurement, 400 MHz), the following values were obtained:

δ=2.50 ppm (s, 12H, H of the methyl group at the quinoline ring)

δ=6.06~8.6 ppm (m, 28H, H of the quinoline ring and the phenyl ring)

In Examples described below, the light yellow powder was used after purification by sublimation.

SYNTHESIS EXAMPLE 6 (CHEMICAL FORMULA 31)

Synthesis of bis(2-methyl-8-quinolinato) aluminum (III)-μ-1,1
-dioxy-1,1-diphenylsilylene-bis(2-methyl-8-quinolinato) aluminum (III)

2-Methyl-8-hydroxyquinoline (Hmhq, a product of Tokyo Kasei Co., Ltd.) in an amount of 1.6 g (0.01 mol) and aluminum isopropoxide (a product of Tokyo Kasei Co., Ltd.) in an amount of 2.0 g (0.01 mol) were added to 80 milliliter of ethanol. The mixture was heated for 30 minutes under stirring and cooled by standing.

Then, 5 g of sodium sulfate was added to the solution obtained and the mixture was stirred and filtered. To the filtrate solution thus obtained, 1.08 g (0.005 mol) of diphenylsilanediol (a product of Lancaster Company) was added and stirred. Then, 1.6 g (0.01 mol) of Hmhq was added. The mixture was heated under stirring and kept refluxing for 5 hours in an oil bath under an argon stream. After cooling the mixture by standing, powder precipitated out was separated by filtration with a reduced pressure, washed with 10 milliliter of ethanol and dried to obtain 2.5 g (0.00278 mol) of light yellow powder.

Yield of the object product was 56%.

As the result of mass spectrometric analysis of the light yellow powder obtained, the following value was obtained: m/Z=899 (M$^+$).

As the result of measurement of proton nuclear magnetic resonance ($^1$H-NMR; reference, tetramethylsilane (TMS); solvent, dimethylsulfoxide (DMSO); wave length of the measurement, 400 MHz), the following values were obtained:

δ=2.35~2.9 ppm (s, 12H, H of the methyl group at the quinoline ring)

δ=6.4~8.5 ppm (m, 30H, H of the quinoline ring and the phenyl ring)

In Examples described below, the light yellow powder was used after purification by sublimation.

EXAMPLE 1

A glass plate (25 mm×75 mm×1.1 mm; a product of HOYA Co., Ltd.) on which an ITO transparent electrode of 100 nm thickness was formed was used as the transparent substrate. The substrate was washed in isopropyl alcohol with ultrasonic wave for 30 minutes and further washed by dipping in isopropyl alcohol. The substrate was dried in a stream of dry nitrogen gas and fixed to a substrate holder of a commercial vacuum vapor deposition apparatus. On the other hand, 200 mg of N,N'-diphenyl-N,N'-bis(4-methylphenyl)(1,1'-biphenyl)-4,4'-diamine (TPDA) was placed in an electrically heated boat made of molybdenum and 200 mg of 4,4'-bis(2,2-diphenylvinyl)biphenyl (DPVBi) was placed in another electrically heated boat made of molybdenum. In still another electrically heated boat made of molybdenum, 200 mg of the compound obtained in Synthesis Example 1 was placed. The boats were attached to the vacuum deposition apparatus.

After evacuating the vacuum chamber to 4×10$^{-4}$ Pa, the boat containing TPDA was electrically heated to 220° C. and the compound was vapor deposited on the transparent substrate at a deposition rate of 0.1 to 0.3 nm/second to form a hole injecting and transporting layer of 60 nm thickness.

Next, the boat containing DPVBi was electrically heated to 240° C. and the compound was vapor deposited on the hole injecting and transporting layer formed above at a deposition rate of 0.1 to 0.3 nm/second to form a light emitting layer of 40 nm thickness.

Then, the boat containing the compound obtained in Synthesis Example 1 was electrically heated to 314° C. and the compound was vapor deposited on the light emitting layer formed above at a deposition rate of 0.1 nm/second to form an electron injecting and transporting layer of 20 nm thickness. Temperature of the substrate at the time of vapor deposition was room temperature.

The vacuum chamber was opened and a mask made of stainless steel was placed on the electron injecting and transporting layer. Magnesium in an amount of 3 g was placed in an electrically heated boat made of molybdenum and silver in an amount of 0.5 g was placed in a basked for vapor deposition made of tungsten. After the vacuum chamber was evacuated to 2×10$^{-4}$ Pa again, the boat containing magnesium was electrically heated and magnesium was vapor deposited at a deposition rate of 1.5 to 2.0 nm/second. At the same time, the basket containing silver was heated and silver was vapor deposited at a deposition rate of 0.1 nm/second. Thus, the opposite electrode made of a mixture of magnesium and silver was formed to prepare the object organic EL device.

Structure of the organic EL device obtained above is shown in FIG. 1.

Using the ITO electrode of this device as the anode and the opposite electrode made of a mixture of magnesium and silver of this device as the cathode, the device was loaded with a direct voltage of 11 volt. Electric current of a density of 5.8 mA/cm$^2$ was observed and blue light (chromaticity coordinates: 0.173, 0.204) was emitted. The emitted light had the maximum wave length of 468 nm, a luminance of 84 cd/m$^2$ and an efficiency of light emission of 0.41 Lumen/W. After loading the voltage for 100 hours in an argon stream, none of cleavage and whitening was observed on the surface of the electrodes and emission of the blue light was still observed.

EXAMPLES 2 TO 5

EL devices were prepared and evaluated by the same method as that in Example 1 except that a compound shown in Table 1 was used as the electron injecting and transporting layer in place of the compound obtained in Synthesis Example 1 and the heating temperature during the vapor deposition was changed to the value shown in Table 1. Results are shown in Table 1.

TABLE 1

(Part 1)

|  | Al chelate compound used | temperature of deposition boat (°C.) | loaded voltage (V) | current density (mA/cm$^2$) | luminance of emitted light (cd/m$^2$) |
| --- | --- | --- | --- | --- | --- |
| Example 2 | Synthesis Example 3 | 412 | 11 | 6.7 | 96 |
| Example 3 | Synthesis Example 4 | 290 | 11 | 8.0 | 112 |
| Example 4 | Synthesis Example 5 | 300 | 11 | 7.4 | 98 |
| Example 5 | Synthesis Example 6 | 320 | 11 | 9.5 | 102 |

(Part 2)

|  | efficiency of light emission (Lumen/W) | peak wave length of emitted light (nm) | adhesion of electrodes | life of device (hour) |
| --- | --- | --- | --- | --- |
| Example 2 | 0.41 | 468 | good | 100 or more |
| Example 3 | 0.40 | 468 | good | 100 or more |
| Example 4 | 0.38 | 467 | good | 100 or more |
| Example 5 | 0.31 | 469 | good | 100 or more |

EXAMPLE 6

An EL device was prepared and evaluated by the same method as that in Example 1 except that the compound obtained in Synthesis Example 4 was used as the material of the light emitting layer in place of DPVBi, tris(8-quinolinato) aluminum (III) was used as the electron injecting and transporting layer and the temperatures of the heated boats during the vapor deposition were changed to 290° C. and 285° C., respectively.

Using the ITO electrode of this device as the anode and the opposite electrode made of a mixture of magnesium and silver of this device as the cathode, the device was loaded with a direct voltage of 12.5 volt. Electric current of a density of 11.6 mA/cm$^2$ was observed and green light (chromaticity coordinates: 0.253, 0.467) was emitted. The emitted light had the maximum wave length of 506 nm, a luminance of 110 cd/m$^2$ and an efficiency of light emission of 0.24 Lumen/W. After loading the voltage for 200 hours in an argon stream, none of cleavage and whitening Was observed on the surface of the electrodes and emission of the green light of a luminance of 55 cd/m$^2$ was observed.

EXAMPLE 7

An EL device was prepared and evaluated by the same method as that in Example 6 except that the compound obtained in Synthesis Example 1 was used as the material of the light emitting layer and the temperature of the heated boat during the vapor deposition was changed to 314° C.

Using the ITO electrode of this device as the anode and the opposite electrode made of a mixture of magnesium and silver of this device as the cathode, the device was loaded with a direct voltage of 11 volt. Electric current of a density of 7.1 mA/cm$^2$ was observed and green light was emitted. The emitted light had the maximum wave length of 507 nm, a luminance of 100 cd/m$^2$ and an efficiency of light emission of 0.4 Lumen/W. After loading the voltage for 200 hours in an argon stream, none of cleavage and whitening was observed on the surface of the electrodes and emission of the green light of a luminance of 50 cd/m$^2$ was still observed.

EXAMPLE 8

An EL device was prepared and evaluated by the same method as that in Example 6 except that the compound obtained in Synthesis Example 2 was used as the material of the light emitting layer and the temperature of the heated boat during the vapor deposition was changed to 330° C.

Using the ITO electrode of this device as the anode and the opposite electrode made of a mixture of magnesium and silver of this device as the cathode, the device was loaded with a direct voltage of 12 volt. Electric current of a density of 10.5 mA/cm$^2$ was observed and bluish green light was emitted. The emitted light had the maximum wave length of 505 nm, a luminance of 120 cd/m$^2$ and an efficiency of light emission of 0.3 Lumen/W. After loading the voltage for 110 hours in an argon stream, emission of the bluish green light of a luminance of 60 cd/m$^2$ was still observed.

COMPARATIVE EXAMPLE 1

An EL device was prepared and evaluated by the same method as that in Example 1 except that bis(2-methyl-8-quinolinolato) (phenolato) aluminum (III) was used as the material of the electron injecting and transporting layer and the temperature of the heated boat during the vapor deposition was changed to 240° C.

Using the ITO electrode of this device as the anode and the opposite electrode made of a mixture of magnesium and silver of this device as the cathode, the device was loaded with a direct voltage of 10 volt. Electric current of a density of 9.5 mA/cm$^2$ was observed and blue light was emitted. The emitted light had the maximum wave length of 475 nm, a luminance of 125 cd/m$^2$ and an efficiency of light emission of 0.41 Lumen/W. After loading the voltage, the emitted light changed to white light from the blue light and the luminance decreased to a half of the initial value after 40 hours.

COMPARATIVE EXAMPLE 2

An EL device was prepared and evaluated by the same method as that in Example 1 except that bis(2-methyl-8-quinolinolato) (p-phenylphenolato) aluminum (III) was used as the material of the electron injecting and transporting layer and the temperature of the heated boat during the vapor deposition was changed to 260° C.

Using the ITO electrode of this device as the anode and the opposite electrode made of a mixture of magnesium and silver of this device as the cathode, the device was loaded with a direct voltage of 10 volt. Electric current of a density of 43.2 mA/cm$^2$ was observed and blue light was emitted. The emitted light had the maximum wave length of 510 nm, a luminance of 105 cd/m$^2$ and an efficiency of light emission of 0.08 Lumen/W. After loading the voltage for 65 hours, the emission of light entirely disappeared.

COMPARATIVE EXAMPLE 3

An EL device was prepared and evaluated by the same method as that in Example 6 except that tris(8-quinolinato) aluminum (III) was used as the material of the electron injecting and transporting layer, bis(2-methyl-8-quinolinato)

aluminum (III)-μ-4,4'-dioxybiphenylene-bis( 2-methyl-8-quinolinato) aluminum (III) having the following formula:

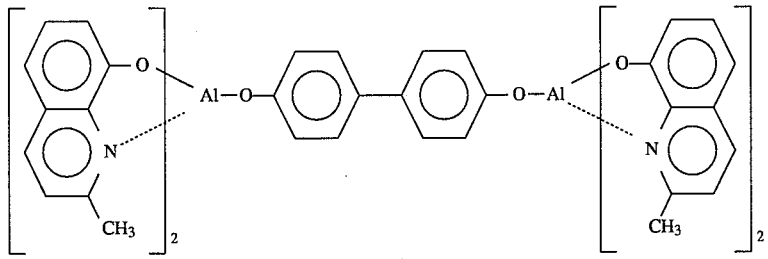

was used as the light emitting layer and the temperature of the heated boat during the vapor deposition was changed to 375° C.

Using the ITO electrode of this device as the anode and the opposite electrode made of a mixture of magnesium and silver of this device as the cathode, the device was loaded with a direct voltage of 10 volt. Electric current of a density of 49.6 mA/cm$^2$ was observed and green light was emitted. The emitted light had the maximum wave length of 506 nm, a luminance of 78 cd/m$^2$ and an efficiency of light emission of 0.05 Lumen/W. After loading the voltage, the emitted light changed to yellowish green light from the green light and the luminance decreased to a half of the initial value after 60 hours.

The above results show that the organic EL device exhibits the excellent properties with respect to the life of light emission and the stability of color of the emitted light when a compound selected from the group of the compounds having the general formula (I) as a component of the device is used.

What is claimed is:

1. An organic electroluminescence device comprising a layer containing a compound having an aluminum complex structure placed between a pair of electrodes wherein said compound is represented by the following general formula (I):

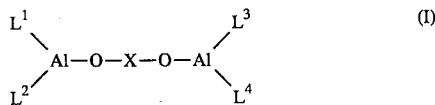

wherein X indicates a group represented by one of the formulae: —Ar$^1$—Y—Ar$^2$—

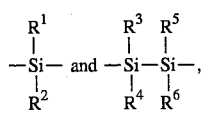

therein Ar$^1$ and Ar$^2$ indicate each independently a substituted or unsubstituted aromatic ting having 6 to 24 carbon atoms, Y is an alkylene group, a cycloalkylene group, an alkylidene group, a cycloalkylidene group, an arylenedioxy group, an alkylenedioxy group,

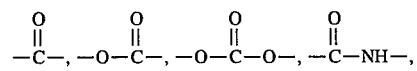

—O—, —S—, —SO— or —SO$_2$—, and R$^1$ to R$^6$ indicate each independently an aryl group having 6 to 12 carbon atoms, an alkyl group having 1 to 12 carbon atoms or a cycloalkyl group having 5 to 12 carbon atoms; and L$^1$ to L$^4$ indicate each independently a substituted or unsubstituted ligand having one of the formulae:

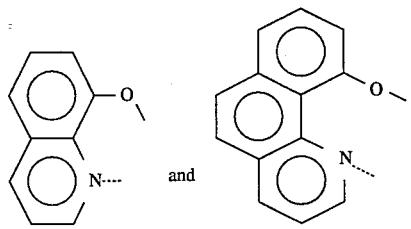

2. The organic electroluminescence device as defined in claim 1 wherein the substituent of said substituted aromatic ring and said substituted ligand in the compound having an aluminum complex structure represented by the general formula (I) is an alkyl or alkoxy group having 1 to 6 carbon atoms, phenyl group, cyclohexyl group, a halogen atom, nitro group or cyano group.

3. The organic electroluminescence device as defined in claim 1 wherein L$^1$ to L$^4$ in the compound having an aluminum complex structure represented by the general formula (I) indicate each a ligand having the formula:

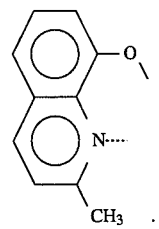

4. The organic electroluminescence device as defined in claim 1 wherein X in the compound having an aluminum complex structure represented by the general formula (I) indicates a group represented by the formula:

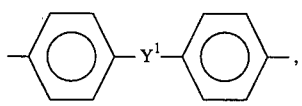

therein $Y^1$ is a group having one of the formulae: —O—, —CH$_2$—,

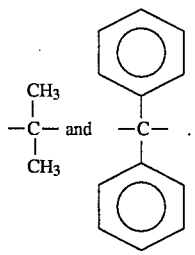

5. The organic electroluminescence device as defined in claim 1 wherein X in the compound having an aluminum complex structure represented by the general formula (I) indicates a group having the formula:

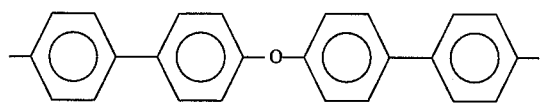

6. The organic electroluminescence device as defined in claim 1 wherein X in the compound having an aluminum complex structure represented by the general formula (I) indicates diphenylsilylene group.

7. The organic electroluminescence device as defined in claim 1 further comprising an electron injecting and transporting layer wherein at least said electron injecting and transporting layer comprises the compound having an aluminum complex structure represented by the general formula (I).

8. The organic electroluminescence device as defined in claim 1 further comprising a light emitting layer wherein at least said light emitting layer comprises the compound having an aluminum complex structure represented by the general formula (I).

9. The organic electroluminescence device as defined in claim 1 further comprising an anode, hole injecting and transporting layer, light emitting layer, electron injecting and transporting layer and cathode wherein one or both of the light emitting layer and the electron injecting and transporting layer comprise the compound having an aluminum complex structure represented by the general formula (I).

10. A compound having an aluminum complex structure represented by the following general formula (I):

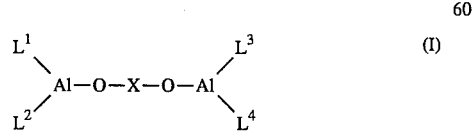

wherein X indicates a group represented by one of the formulae: —Ar$^1$—Y—Ar$^2$—,

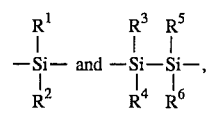

therein Ar$^1$ and Ar$^2$ indicate each independently a substituted or unsubstituted aromatic ring having 6 to 24 carbon atoms, Y is an alkylene group, a cycloalkylene group, an alkylidene group, a cycloalkylidene group, an arylenedioxy group, an alkylenedioxy group,

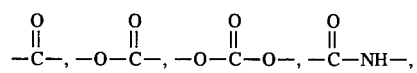

—O—, —S—, —SO— or —SO$_2$—, and R$^1$ to R$^6$ indicate each independently an aryl group having 6 to 12 carbon atoms, an alkyl group having 1 to 12 carbon atoms or a cycloalkyl group having 5 to 12 carbon atoms; and L$^1$ to L$^4$ indicate each independently a substituted or unsubstituted ligand having one of the formulae:

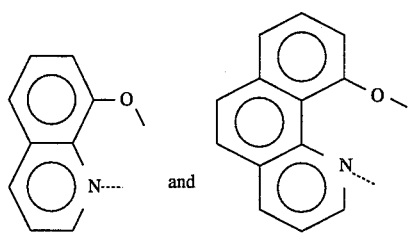

11. The compound having an aluminum complex structure as defined in claim 10 wherein the substituent of said substituted aromatic ring and said substituted ligand in the general formula (I) is an alkyl or alkoxy group having 1 to 6 carbon atoms, phenyl group, cyclohexyl group, a halogen atom, nitro group or cyano group.

12. The compound having an aluminum complex structure as defined in claim 10 wherein L$^1$ to L$^4$ in the general formula (I) indicate each a ligand having the formula:

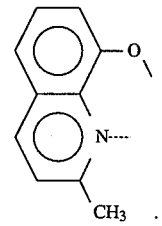

13. The compound having an aluminum complex structure as defined in claim 10 wherein X in the general formula (I) indicates a group represented by the formula:

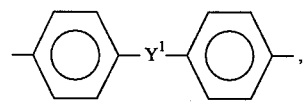

therein $Y^1$ is a group having one of the formulae: —O—, —CH$_2$—,

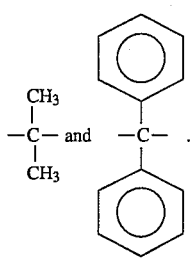
14. The compound having an aluminum complex structure as defined in claim 10 wherein X in the general formula (I) indicates a group having the formula:
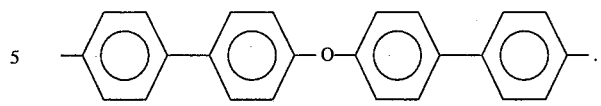
15. The compound having an aluminum complex structure as defined in claim 10 wherein X in the general formula (I) indicates diphenylsilylene group.
* * * * *